United States Patent [19]

Podraza

[11] Patent Number: 5,137,035
[45] Date of Patent: Aug. 11, 1992

[54] BENZOFURANONE COMPOUNDS, AND PRODUCTION OF SMOKING COMPOSITIONS CONTAINING A BENZOFURANONE FLAVORANT ADDITIVE

[75] Inventor: Kenneth F. Podraza, Richmond, Va.

[73] Assignees: Philip Morris Incorporated, New York, N.Y.; Philip Morris Products Inc., Richmond, Va.

[21] Appl. No.: 496,584

[22] Filed: Mar. 21, 1990

[51] Int. Cl.$^5$ .................. A24B 3/12; C07D 313/08
[52] U.S. Cl. ............................. 131/277; 549/270; 549/265
[58] Field of Search .................. 549/270, 265, 269; 131/275, 276, 277

*Primary Examiner*—V. Millin
*Attorney, Agent, or Firm*—James E. Schardt; George A. Depaoli

[57] ABSTRACT

This invention provides a process for the production of novel smoking compositions which contain a benzofuranone flavorant additive, and further provides novel benzofuranone compounds as illustrated by the cis 6-phenyl-3a, 4,5,7a-tetrahydro-2(3H)-benzofuranone:

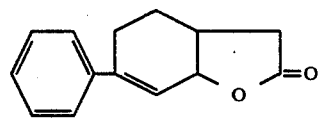

Under normal cigarette smoking conditions, the benzofuranone additive in an invention smoking composition enhances the flavor and aroma of the mainstream and sidestream smoke.

10 Claims, No Drawings

BENZOFURANONE COMPOUNDS, AND PRODUCTION OF SMOKING COMPOSITIONS CONTAINING A BENZOFURANONE FLAVORANT ADDITIVE

BACKGROUND OF THE INVENTION

A variety of flavorants have been developed and proposed for incorporation into tobacco products Illustrative of such tobacco flavorants are those described in U.S. Pat. Nos. 3,580,259; 3,625,224; 3,722,516; 3,750,674; 3,879,425; 3,881,025; 3,884,247; 3,890,981; 3,903,900; 3,914,451; 3,915,175; 3,920,027; 3,924,644; 3,937,228; 3,943,943; 3,586,387; 4,379,754; and the like.

J. C. Leffingwell et al "Tobacco Flavoring For Smoking Products" (R. J. Reynolds publication, 1972) includes a listing of desirable flavorants for smoking compositions.

Of specific interest with respect to the present invention is the proposed utilization of lactone compounds as flavorants in tobacco products Various lactones are known to contribute desirable properties to the flavor and aroma of tobacco products under smoking conditions.

U.S. Pat. No. 3,251,366 describes tobacco products that contain a lactone flavorant additive such as $\alpha,\beta$-dimethyl-$\gamma$-pentyl-$\gamma$-hydroxybutenolide which imparts a celery-like note to mainstream smoke.

U.S. Pat. No. 3,372,699 and U.S. Pat. No. 3,372,700 describe the use of a lactone such as $\beta$-methylbutyrolactone or 4-hydroxy-4-methyl-5-hexenoic acid $\gamma$ lactone as a flavorant additive in tobacco products.

U.S. Pat. No. 3,380,457; U.S. Pat. No. 3,563,248; and U.S. Pat. No. 3,861,403 describe other lactones which are recommended for use as flavorant additives in tobacco products, such as $\beta$-methyl-$\delta$-valerolactone, 3-(2-hydroxycyclohexyl)propionic acid $\delta$ lactone, 4-methyl-6-n-pentyl-$\alpha$-pyrone, and the like.

There is continuing research effort to develop improved smoking compositions which generate mainstream smoke with flavorant additive-enhanced taste and aroma under smoking conditions.

Accordingly, it is an object of this invention to provide smoking compositions having incorporated therein a flavorant additive component which is characterized by lack of undesirable mobility and/or volatility at ambient temperature.

It is another object of this invention to provide smoking compositions having incorporated therein a flavorant additive which under normal smoking conditions imparts improved flavor to mainstream smoke and improved aroma to sidestream smoke.

It is a further object of this invention to provide novel benzofuranone compounds which are adapted to be incorporated into cigarette fillers as flavorant additives, and which under normal smoking conditions are volatilized into the cigarette smoke.

Other objects and advantages of the present invention shall become apparent from the following description and examples

DESCRIPTION OF THE INVENTION

One or more objects of the present invention are accomplished by the provision of a smoking composition comprising an admixture of (1) combustible filler selected from natural tobacco, reconstituted tobacco and tobacco substitutes, and (2) between about 0.0001–5 weight percent, based on the total weight of filler, of a benzofuranone additive corresponding to the formula:

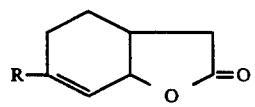

where R is a $C_1$–$C_{10}$ hydrocarbyl substituent, such as a $C_1$–$C_6$ or $C_6$–$C_{10}$ aromatic radical.

Illustrative of the R substituent are radicals which include methyl, ethyl, ethenyl, propyl, 2-propyl, butyl, 2-butyl, isobutyl, pentyl, hexyl, 2-hexyl, 2-hexenyl, heptyl, octyl, cyclopentyl, cyclohexyl, cyclohexenyl, phenyl, tolyl, xylyl, and the like.

Preparation Of Tetrahydrobenzofuranones

A general procedure for the preparation of a present invention benzofuranone derivative involves the cyclization of a 6-(carbalkoxymethyl)-2-cyclohexen-1-one in the presence of a metal alkoxide reagent:

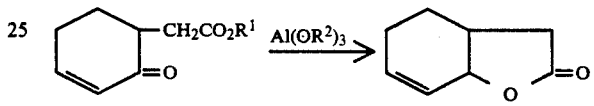

Cis 3a,4,5,7a-tetrahydro-2(3H)-benzofuranone is a known compound, and its synthesis is illustrated in Example I.

Cis 6-methyl-3a,4,5,7a-tetrahydro-2(3H)-benzofuranone is a known compound, and its synthesis is illustrated in Example II. In J. Org. Chem., 46, 3896 (1981) by P. A. Bartlett et al, the synthesis of this compound is accomplished by an alternative route via cis 6-methyl-2-cyclohexenol and cis (4-methyl-2-cyclohexenyl)acetic acid intermediates. The publication disclosure does not contemplate the potential utility of the synthesized benzofuranone derivative as a prospective flavorant additive in smoking products.

The present invention benzofuranone derivatives are stable compounds at ambient temperature. An invention benzofuranone compound, when incorporated in a smoking composition, enhances the flavor and aroma of low delivery cigarette smoke, as demonstrated in Example VI of the present specification.

Preparation Of Smoking Compositions

In a further embodiment this invention provides a method of preparing a smoking composition which is adapted to impart flavor and aroma to mainstream and sidestream smoke under smoking conditions, which method comprises incorporating into natural tobacco, reconstituted tobacco or tobacco substitute between about 0.0001–5 weight percent, based on composition weight, of a benzofuranone flavorant additive corresponding to the formula:

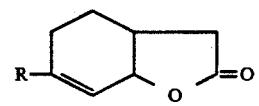

where R is a $C_1$–$C_{10}$ hydrocarbyl substituent.

An invention benzofuranone flavorant additive can be incorporated into the tobacco or tobacco substitute in accordance with methods known and used in the art. Preferably the flavorant additive is dissolved in a solvent such as alcohol or aqueous alcohol and then sprayed or injected into the tobacco and/or tobacco substitute matrix. Such method ensures an even distribution of the flavorant additive throughout the filler, and thereby facilitates the production of a more uniform smoking composition. Alternatively, the flavorant additive may be incorporated as part of a concentrated tobacco extract which is applied to a fibrous tobacco web as in the manufacture of reconstituted tobacco. Another suitable procedure is to incorporate the flavorant additive in tobacco or tobacco substitute filler in a concentration between about 0.5-5 weight percent, based on the weight of filler, and then subsequently to blend the treated filler with filler which does not contain flavorant additive.

The term "tobacco substitute" is meant to include non-tobacco smoking filler materials such as are disclosed in U.S. Pat. Nos. 3,703,177; 3,796,222; 4,019,521; 4,079,742; and references cited therein; incorporated herein by reference.

U.S. Pat. No. 3,796,222 describes a smoking product derived from coffee bean hulls. The hulls are treated with reagents that attack the alkaline earth metal cross-links causing the release of the coffee pectins The pectins act as a binding agent and together with the treated hulls may be handled and used similarly to a tobacco product.

U.S. Pat. No. 4,019,521 discloses a process for forming a smoking material which involves heating a cellulosic or carbohydrate material at a temperature of 150°-750° C. in an inert atmosphere for a period of time sufficient to effect a weight loss of at least 60 percent but not more than 90 percent.

U.S. Pat. No. 4,079,742 discloses a process for the manufacture of a synthetic smoking product from a cellulosic material, which process involves a pyrolysis step and a basic extraction step to yield a resultant matrix which has a tobacco-like brown color and has improved smoking characteristics.

The following Examples are further illustrative of the present invention. The specific ingredients and processing parameters are presented as being typical, and various modifications can be derived in view of the foregoing disclosure within the scope of the invention.

EXAMPLE I cis 3a,4,5,7a-Tetrahydro-2(3H)-benzofuranone

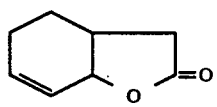

To a solution of 13.5 g (66.0 mmoles) of aluminum isopropoxide in 100 ml of toluene was added 2.0 g (11.0 mmoles) of 6-(carbethoxymethyl)-2-cyclohexen-1-one at room temperature, and the solution was heated to 90° C. for 18 hours. The solution was cooled to room temperature, and aqueous saturated sodium hydrogen tartrate and ethyl acetate were added. The aqueous layer was extracted with ethyl acetate, and the combined ethyl acetate extracts were dried over anhydrous magnesium sulfate and evaporated under reduced pressure. The crude material was purified by Kugelrohr distillation (bp 40°-80° C./0.01 mm Hg) to yield 1.3 g (86%) of cis 3a,4,5,7a-tetrahydro-2(3H)-benzofuranone, as confirmed by NMR and IR data.

EXAMPLE II cis 6-Methyl-3a,4,5,7a-tetrahydro-2(3H)-benzofuranone

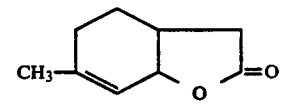

The reaction of 18.73 g (91.7 mmoles) of aluminum isopropoxide in 150 ml of toluene with 3.0 g (15.3 mmoles) of 6-(carbethoxymethyl)-3-methyl-2-cyclohexen-1-one was conducted in a similar manner to the synthesis of 3a,4,5,7a-tetrahydro-2(3H)-benzofuranone described in Example I. The crude material was purified by Kugelrohr distillation (bp 55°-80° C./0.01 mm Hg) to yield 1.7 g (74%) of cis 6-methyl-3a,4,5,7a-tetrahydro-2(3H)-benzofuranone, as confirmed by NMR and IR data.

EXAMPLE III

This Example illustrates the preparation of cis 6-n-butyl-3a,4,5,7a-tetrahydro-2(3H)-benzofuranone as a novel compound in accordance with the present invention.

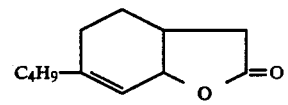

The reaction of 7.71 g (37.8 mmoles) of aluminum isopropoxide in 100 ml of toluene with 1.5 g (6.3 mmoles) of 6-(carbethoxymethyl)-3-n-butyl-2-cyclohexen-1-one was conducted in a similar manner to the synthesis of 3a,4,5,7a-tetrahydro-2(3H)-benzofuranone as an oil NMR and IR confirm the structure of the compound.

Anal. Calc. for $C_{12}H_{18}O_2$: C,74.19; H,9.34. Found: C,74.41; H,9.46.

EXAMPLE IV

This Example illustrates the preparation of cis 6-phenyl-3a,4,5,7a-tetrahydro-2(3H)-benzofuranone as a novel compound in accordance with the present invention.

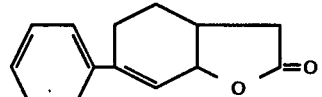

The reaction of 7.12 g (34.8 mmoles) of aluminum isopropoxide in 100 ml of toluene with 1.5 g (5.8 mmoles) of 6-(carbethoxymethyl)-3-n-butyl-2-cyclohexen-1-one was conducted in a similar manner to the synthesis of 3a,4,5,7a-tetrahydro-2(3H)-benzofuranone described in Example I. The crude material was purified by crystallization from hexane to yield 1.04 g (84%) of cis 6-phenyl-3a,4,5,7a-tetrahydro-2(3H)-benzofuranone, mp 90°-92° C. NMR and IR confirm the structure of the compound.

Anal. Calc. for $C_{14}H_{14}O_2$: C,78.48; H,6.59. Found: C,78.24; H,6.55.

EXAMPLE V

This Example illustrates the subjective evaluation of the aroma properties of the Examples I–IV compounds by a panel of experts[1]. (1) A test tetrahydrobenzofuranone was placed in a capped bottle. The panel evaluated the compound at room temperature by removing the bottle cap and sniffing the aroma emitted by the contained material.

| EXAMPLE COMPOUND | AROMA PROPERTIES |
| --- | --- |
| I. cis 3a,4,5,7a-tetrahydro-2(3H)-benzofuranone | fruity, sweet, spicy |
| II. cis 6-methyl-3a,4,5,7a-tetrahydro-2(3H)-benzofuranone | fruity, sweet, coconut, woody, vanilla |
| III. cis 6-n-butyl-3a,4,5,7a-tetrahydro-2(3H)-benzofuranone | waxy, fruity, sweet |
| IV. cis 6-phenyl-3a,4,5,7a-tetrahydro-benzofuranone | fruity, woody |

EXAMPLE VI

This Example illustrates the subjective evaluation of the flavorant properties of the Examples I–IV compounds[1]. (1) Cigarettes are fabricated employing a blend of tobaccos treated with an ethanolic solution of a flavorant compound to provide 0.05% of the compound by weight of the tobacco. The cigarettes are targeted to deliver 8 mg of tar per cigarette.

Untreated controls are prepared and the treated cigarettes are compared to the controls by an experienced smoking panel.

| EXAMPLE COMPOUND | FLAVOR PROPERTIES |
| --- | --- |
| I. cis 3a,4,5,7a-tetrahydro-2(3H)-benzofuranone | no difference |
| II. cis 6-methyl-3a,4,5,7a-tetrahydro-2(3H)-benzofuranone | sweet, coconut |
| III. cis 6-n-butyl-3a,4,5,7a-tetrahydro-2(3H)-benzofuranone | waxy, slight green |
| IV. cis 6-phenyl-3a,4,5,7a-tetrahydro-2(3H)-benzofuranone | sweet, coconut |

What is claimed is:

1. A smoking composition comprising an admixture of (1) combustible filler selected from natural tobacco, reconstituted tobacco and tobacco substitutes, and (2) between about 0.0001–5 weight percent, based on the total weight of filler, of a benzofuranone additive corresponding to the formula:

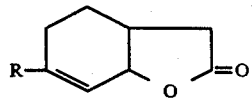

where R is a $C_1$–$C_{10}$ hydrocarbyl substituent.

2. A smoking composition in accordance with claim 1 wherein the tobacco substitutes are selected from pectinaceous, cellulosic and carbohydrate materials.

3. A smoking composition in accordance with claim 1 wherein the hydrocarbyl substituent is a $C_1$–$C_6$ alkyl group.

4. A smoking composition in accordance with claim 1 wherein the hydrocarbyl substituent is a $C_6$–$C_{10}$ aromatic group.

5. A smoking composition in accordance with claim 1 wherein the benzofuranone additive is cis 6-methyl-3a,4,5,7a-tetrahydro-2(3H)-benzofuranone.

6. A smoking composition in accordance with claim 1 wherein the benzofuranone additive is cis 6-n-butyl-3a,4,5,7a-tetrahydro-2(3H)-benzofuranone.

7. A smoking composition in accordance with claim 1 wherein the benzofuranone additive is cis 6-phenyl-3a,4,5,7a-tetrahydro-2(3H)-benzofuranone.

8. A method of preparing a smoking composition which is adapted to impart flavor and aroma to mainstream and sidestream smoke under smoking conditions, which method comprises incorporating into natural tobacco, reconstituted tobacco or tobacco substitute between about 0.0001–5 weight percent, based on composition weight, of a benzofuranone flavorant additive corresponding to the formula:

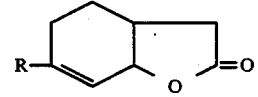

wherein R is a $C_1$–$C_{10}$ hydrocarbyl substituent.

9. cis 6-n-Butyl-3a,4,5,7a-tetrahydro-2(3H)-benzofuranone.

10. cis 6-Phenyl-3a,4,5,7a-tetrahydro-2(3H)-benzofuranone.

* * * * *

UNITED STATES PATENT AND TRADEMARK OFFICE
CERTIFICATE OF CORRECTION

PATENT NO. : 5,137,035
DATED : August 11, 1992
INVENTOR(S) : Kenneth F. Podraza

It is certified that error appears in the above-indentified patent and that said Letters Patent is hereby corrected as shown below:

Cols. 3,4 & 5

In Examples I-VI, all occurrences, "as" in compound nomenclature should be underlined --*cis*--.

Col. 4

In Example III, the descriptive text is incomplete and should read as follows:

--The reaction of 7.71 g (37.8 mmoles) of aluminum isopropoxide in 100 ml of toluene with 1.5 g (6.3 mmoles) of 6-(carbethoxymethyl)-3-n-butyl-2-cyclohexen-1-one was conducted in a similar manner to the synthesis of 3a,4,5,7a-tetrahydro-2(3H)-benzofuranone described in Example I. The crude material was purified by Kugelrohr distillation (bp 50°-80°C/0.02 mm Hg), followed by chromatography on silica gel eluted with 20% ethyl acetate in hexane to yield 0.40 g (33%) of *cis* 6-n-butyl-3a,4,5,7a-tetrahydro-2(3H)-benzofuranone as an oil. NMR and IR confirm the structure of the compound.--

Signed and Sealed this

Second Day of November, 1993

Attest:

BRUCE LEHMAN

Attesting Officer

Commissioner of Patents and Trademarks